(12) United States Patent
Araki et al.

(10) Patent No.: US 7,550,437 B2
(45) Date of Patent: Jun. 23, 2009

(54) COMPOSITIONS FOR PREVENTING AND TREATING DIGESTIVE ORGANS DISEASES

(75) Inventors: Hiromasa Araki, Nara (JP); Atsufumi Kawabata, Nara (JP); Ryotaro Kuroda, Osaka (JP); Kazuaki Kakehi, Nara (JP); Shuichi Tanaka, Osaka (JP); Kenzo Kawai, Osaka (JP); Sachiyo Nishimura, Nara (JP); Hiroyuki Nishikawa, Nara (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 707 days.

(21) Appl. No.: 11/322,254

(22) Filed: Jan. 3, 2006

(65) Prior Publication Data

US 2006/0172949 A1     Aug. 3, 2006

Related U.S. Application Data

(62) Division of application No. 10/204,555, filed as application No. PCT/JP01/01188 on Feb. 20, 2001, now abandoned.

(30) Foreign Application Priority Data

Feb. 24, 2000  (JP) ............................. 2000-047515

(51) Int. Cl.
*A61K 38/08*   (2006.01)
(52) U.S. Cl. ....................................................... 514/17
(58) Field of Classification Search ........................ None
See application file for complete search history.

(56) References Cited

U.S. PATENT DOCUMENTS 5,541,116 A * 7/1996 Bergmann .................. 436/176

FOREIGN PATENT DOCUMENTS

DE          41 32 587        5/1993

OTHER PUBLICATIONS

Vergnolle et al., Proc. Natl. Acad. Sci. USA, 1998, vol. 95, pp. 7766-7771.*
Abstract for JP 11 171791, Kaneka Corp (Jun. 29, 1999), Database WPI, Section Ch, Week 199963, Derwent Publications Ltd., London, GB; AN 1999-424910, XP002230573.
Corvera et al., "Thrombin and Mast Cell Tryptase Regulate Guinea-Pig Myenteric Neurons Through Proteinase-Activated Receptors-1 and -2", *Journal of Physiology*, vol. 517, No. 3, pp. 741-756 (Jun. 15, 1999).
Shirai, Takayuki. "I, Juunishichou Kaiyou," Medicina (1994), vol. 31, No. 1, pp. 30-34.
McConalogue, K. et al. "Expression and Cellular Localization of Proteinase-Activated Receptor-2 (PAR-2) in the Gastrointestinal Tract," Gastroenterology (1997) vol. 112, No. 4 suppl., p. A1171.
Vergnolle et al., "Proteinase-Activated Receptor 2 ($PAR_2$)-activating Peptides: Identification of a Receptor Distinct from $PAR_2$ that Regulates Intestinal Transport", *Proc. Natl. Acad. Sci. USA*, vol. 95, pp. 7766-7771 (Jun. 1998).
Kawabata, Atsushi et al. "Protease Juyoutai (PAR) no Seiriteki Yakuwari: tokuni Shoukaki kei Kinou e no Kanyo ni tsuite," Nippon Yakurigaku Zasshi (1999), vol. 114, Suppl. 1, pp. 173-179.

* cited by examiner

*Primary Examiner*—Cecilia J. Tsang
*Assistant Examiner*—Roy Teller
(74) *Attorney, Agent, or Firm*—Browdy and Neimark, P.L.L.C.

(57) ABSTRACT

The present invention provides a composition for safely and effectively preventing and treating digestive organs diseases, particularly, gastric ulcer, duodenal ulcer, gastritis, diarrhea, enteritis and the like. There is also provided a composition having a novel mechanism of action in order to solve the problems which was difficult to be solved by the side effect previously known mechanisms of action. More particularly, there is provided a pharmaceutical composition containing an ingredient which activates PAR-2 as an essential ingredient, which is useful for inhibiting gastric acid secretion, promoting digestive tract mucus secretion, protecting digestive tract mucosa, repairing tissue of digestive organs, and preventing and treating digestive organs diseases.

9 Claims, 4 Drawing Sheets

COMPOSITIONS FOR PREVENTING AND TREATING DIGESTIVE ORGANS DISEASES

This is a division of parent application Ser. No. 10/204,555, filed Aug. 22, 2002.

FIELD OF THE INVENTION

The present invention relates to compositions for preventing and treating digestive organs diseases, especially, compositions for preventing and/or treating gastric ulcer, duodenal ulcer, gastritis, diarrhea, enteritis and the like.

BACKGROUND OF THE INVENTION

Peptic ulcer such as gastric ulcer, duodenal ulcer and the like are resulted from the disruption of a balance between aggressive factors and protective factors. Examples of disruption-inducing factors include drugs (e.g., non-steroidal anti-inflammatory agents, adrenocortical hormone agents, antibiotics, anti-cancer agents, oral hypoglycemic agents), stress, alcohols, corrosive drugs, cirrhosis, anisakid spp., eating habits and the like. At present, aggressive factor inhibitors, protective factor enhancers, and combinations thereof are clinically used.

As the aggressive factor inhibitors, there are clinically used antacids (e.g., sodium bicarbonate and aluminum hydroxide gel, magnesium oxide etc.), anticholinergics (e.g., atropine sulfate, pirenzepine hydrochloride etc.), H2-receptor antagonists (e.g., cimetidine, ranitidine, famotidine, nizatidine, roxatidine etc.), proton pump inhibitors (e.g., omepurazor, ransoprazol, ransoprazol sodium etc.), anti-gastrin drugs (e.g., proglumide, secretin, urogastorone), and anti-pepsin drugs (sucrose sulfate ester, sucralfate etc.) and the like.

As the protective factor enhancers, there are clinically used mucosal protective drugs (e.g., sucralfate, rebamipide, teprenone etc.), mucosal covering drugs (e.g., sodium arginate, azunol preparation etc.), tissue repair accelerating drugs (e.g., aceglutamide aluminum, aldioxa, gefalnate etc.), mucus production accelerating drugs (e.g., proglumide, teprenone, secretin, aldioxa etc.), mucosal microcirculation improving drugs (e.g., cetraxate hydrochloride, benexate, sulpirid etc.), prostaglandin synthesis accelerating drugs (e.g., sofalcone) and prostaglandin preparations (e.g., ornoprostil, misoprostol, enprostil etc.) and the like. For chronic gastritis, digestive tract function improving drugs (e.g., cisapride, aclatonium napadisilate, bethanechol, domperidone, metoclopramide, trimebutine maleate) are also used.

Aggressive factor inhibitors, H2-receptor antagonists, proton pump inhibitors and the like are widely used because of having a potent gastric acid secretion-inhibiting activity and a prominent therapeutic effect. However, it has been revealed that there are high frequently a rebound of gastric acid secretion, and recurrence or exacerbation of ulcer when a drug administration is stopped even after completely cured once. Further, there were problems that there are ulcers which are not completely cured by a H2-receptor antagonist, and that hyperplasia of an enterochromaffin-like cell, hypergastrinemia, appearance of gastric carcinoid and the like are reported depending on use of a proton pump inhibitor and, thus, its dose is limited. While the protective factor enhancers have more mild actions as compared with the above aggressive factor inhibitors, their therapeutic effects were subsidiary. Therefore, patients having digestive organs disease and physicians have desired development of an aggressive factor inhibitor or a protective factor enhancer, which is neither a H2-receptor antagonist nor a proton pump inhibitor and can be safely and effectively used through other mechanism of action.

Meanwhile, it is known that PAR (protease-activated receptor) belongs to a seven-transmembrane type G protein coupling receptor, and is a receptor activated by a protease (Hollenberg, M. D., Trends Pharmacol. Sci., 17, 3-6, 1996 Hollenberg, M. D., Trends Pharmacol. Sci., 20, 271-273, 1999). PAR is cleaved by a protease at a specific N-terminal site of an extracellular domain, to expose a new N-terminus. It is believed that the newly exposed N-terminus becomes a chain ligand and is bound to its own activation site, whereby, activation of receptor is caused (Hollenberg, M. D., Trends Pharmacol. Sci., 17, 3-6, 1996 Hollenberg, M. D., Trends Pharmacol. Sci., 20, 271-273, 1999 Vu, T. K. et al., Cell, 64, 1057-68, 1991).

It is reported that subtypes of PAR-1, PAR-2, PAR-3, and PAR-4 exist in PAR, and that their functions differ from each another. It is found that PAR-1, PAR-3, and PAR-4 are activated by thrombin (Vu, T. K. et al., Cell, 64, 1057-1063, Hollenberg, M. D., Trends Pharmacol. Sci., 17, 3-6, 1996 Ishihara, H. et al., Nature, 386, 502-6, 1997 Kahn, M. L. et al., Nature, 394, 690-4, 1998 Xu, W. F. et al., Proc. Natl. Acad. Sci. USA, 95, 6642-6, 1998), and PAR-2 is activated by trypsin (Nystedt, S. et al., Proc. Natl. Acad. Sci. USA, 91, 9208-12, 1994 Molino, M. et al., J. Biol. Chem., 272, 6011-7, 1997) and tryptase (Molino, M. et al., J. Biol. Chem., 272, 6011-7, 1997 Fox, M. T. et al., FEBS Lett, 417, 267-9, 1997).

It is also known that there is a cleavage site on an amino acid sequence of the PAR-1 (Vu, T. K. et al., Cell, 64, 1057-1063, 1991), PAR-2 (Nystedt, S. et al., Proc. Natl. Acad. Sci. USA, 91, 9208-12, 1994), RAR-3 (Ishihara, H. et al., Nature, 386, 502-6, 1997) and PAR-4 (Kahn, M. L. et al., Nature, 394, 690-4, 1998 Xu, W. F. et al., Proc. Natl. Acad. Sci. USA, 95, 6642-6, 1998), and with respect to PAR-1, PAR-2 and PAR-4, the receptor is activated by exogenously adding a synthetic peptide consisting of five or six amino acids synthesized on the basis of an active amino acid sequence of a cleavage site (Vu, T. K. et al., Cell, 64, 1057-68, 1991 Nystedt, S. et al., Proc. Natl. Acad. Sci. USA, 91, 9208-12, 1994 Ishihara, H. et al., Nature, 386, 502-6, 1997 Kahn, M. L. et al., Nature, 394, 690-4, 1998 Xu, W. F. et al., Proc. Natl. Acad. Sci. USA, 95, 6642-6, 1998 Dery, O. et al., Am. J. Physiol., 274, C1429-52, 1998).

As one of the intracellular signals mediated by PAR-2, activation of inositol 1,4,5-triphosphate (IP3) and protein kinase C system are known (Hollenberg, M. D., Trends Pharmacol. Sci., 20, 271-273, 1999 Dery, O. et al., Am. J. Physiol., 274, C1429-52, 1998 Zheng, X. L. et al., J Pharmacol Exp Ther, 285, 325-34, 1998).

With respect to PAR-2, it is reported that there are inflammatory responses (Cirono, G. et al., J. Exp. Med., 183, 821-827, 1996 Kawabata, A et al., Br. J. Pharmacol., 125, 419-422, 1998), constricting and relaxing actions in trachea (Saifeddine, M. et al., Br. J. Pharmacol., 118, 521-531, 1996 Moffatt, J. D. et al., Br. J. Pharmacol., 125, 591-594, 1998 Cocks, T. M. et al., Nature, 398, 156-160, 1999 Hollenberg, M. D. et al., Can. J. Physiol. Pharmacol., 75, 832-884, 1997), and that PAR-2 is expressed in prostate gland, small intestine, colon, liver, kidney, and pancreas (Stephan, K. B. et al., Biochem. J., 341, 1009-1016, 1996).

However, there have not been reported to date on digestive organ system, such as a gastric acid secretion inhibiting action, a mucus secretion promoting action and a mucosal protecting action of PAR-2.

OBJECT OF THE INVENTION

The present invention was done in view of the aforementioned prior art, and an object of the invention is to provide safe and effective compositions for a preventing and treating digestive organs diseases, especially, compositions for preventing and/or treating gastric ulcer, duodenum ulcer, gastritis, diarrhea, enteritis and the like.

Another object is to provide compositions described above having a novel mechanism of action in order to solve the problem that was difficult to be solved by the side effect previously known mechanisms of action.

SUMMARY OF THE INVENTION

The present inventors studied in order to develop a preferred drug in a composition for treating and/or preventing digestive organs disease, especially gastric ulcer, duodenum ulcer, gastritis, diarrhea, enteritis and the like, and intensively researched for finding out new mechanisms of action. Consequently, we first found out that an ingredient which activates PAR-2 (agonist) has an action on digestive system, that is, the ingredient inhibits gastric acid, promotes digestive tract mucus secretion, and has mucosal protective action, which resulted in completion of the present invention.

Thus, the present invention provides:

(1) a composition for inhibiting gastric acid secretion, comprising an ingredient which activates PAR-2;

(2) a composition for promoting gastrointestinal mucus secretion, comprising an ingredient which activates PAR-2;

(3) a composition for protecting gastrointestinal mucosa, comprising an ingredient which activates PAR-2;

(4) a composition for preventing or treating digestive organs diseases, comprising an ingredient which activates PAR-2;

(5) the composition according to (4), wherein the digestive organs disease is the disease selected from gastric ulcer, duodenal ulcer, gastritis, diarrhea, and enteritis;

(6) the composition according to any one of (1)-(5), wherein the ingredient is a peptide;

(7) the composition according to (6), wherein the peptide comprises at least one sequence selected from the group consisting of Ser-Leu-Ile-Gly-Arg-Leu-NH$_2$ (SEQ ID NO: 1) and trans-cinnamoyl-Leu-Ile-Gly-Arg-Leu-ornithine-NH$_2$ (SEQ ID NO: 2);

(8) the composition according to any one of (1)-(5), wherein the ingredient is a protein;

(9) the composition according to (8), wherein the protein is at least one selected from trypsin and tryptase;

(10) the composition according to any one of (1)-(9), which is combined with an inhibitory substance which inhibits an activity of substance for inactivating or degrading the ingredient;

(11) the composition according to (10), which is used together with an inhibitory substance which inhibits an activity of substance for inactivating or degrading the ingredient;

(12) the composition according to (10), which is incorporated with an inhibitory substance which inhibits an activity of substance for inactivating or degrading the ingredient;

(13) the composition according to any one of (10)-(12), wherein the inhibitory substance is a peptidase inhibitor;

(14) the composition according to (13), wherein the peptidase inhibitor is amastatin; and

(15) the composition according to any one of (1)-(14), which is formulated into a DDS preparation.

DETAILED DESCRIPTION OF THE INVENTION

Figure 1:
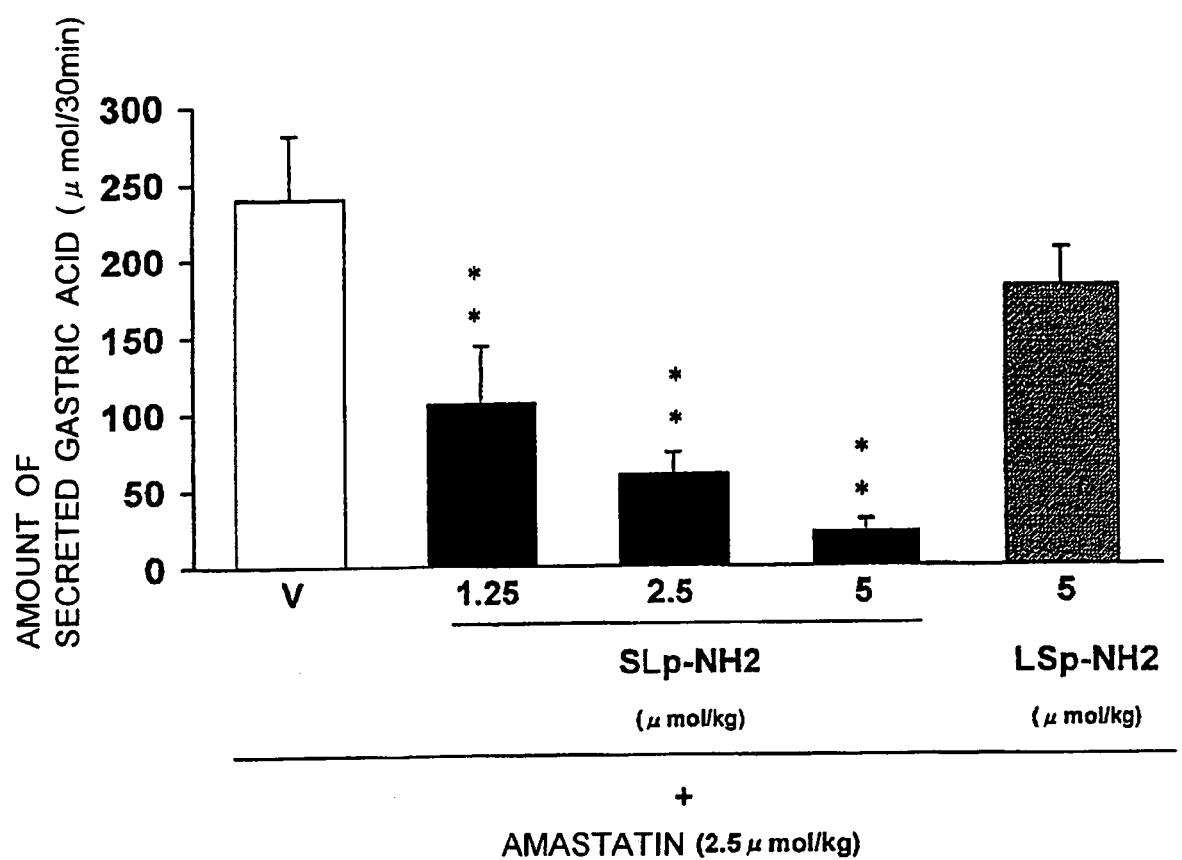
FIG. 1 is a view showing the gastric acid secretion inhibiting effect of a PAR-2 agonist peptide on acceleration of carbachol-inducing gastric acid secretion in vivo. ** $P<0.01$ vs. V (Tukey's test).

An "ingredient which activates PAR-2" refers to any naturally occurring or artificially synthesized substance which has the ability to activate PAR-2 and includes a peptide, a protein, other compounds and the like. More specifically, examples of the ingredient which activates PAR-2 include trypsin and tryptase which are natural PAR-2 activating proteins, the peptide Ser-Phe-Leu-Leu-Arg-NH$_2$ (SEQ ID NO: 3)(hereinafter, referred to as "SFp-NH$_2$") which is synthesized based on the previously reported amino acid sequence of human PAR-1 (Vu, T. K. et al., Cell, 64(6), 1057-1068, 1991), which is known to have an agonist activity on human PAR-1 (Hollenberg, M. D., Molec. Pharmacol., 43, 921-930, 1993 Hollenberg, M. D., Trends Pharmacol. Sci., 17, 3-6, 1996) and have a week agonist activity on PAR-2 (Kawabata, A. et al., J. Pharmacol. Exp. Ther., 288, 358-70, 1999), the peptide Ser-Leu-Ile-Gly-Arg-Leu-NH$_2$ (SEQ ID NO: 1) (hereinafter, referred to as "SLp-NH$_2$")(Hollenberg, M. D., Trends Pharmacol. Sci., 17, 3-6, 1996 Nystedt, S. et al., Proc. Natl. Acad. Sci. USA, 91, 9208-12, 1994) which is synthesized based on amino acid sequence of rat PAR-2 (Saifeddine, M. et al., Br. J. Pharmacol., 118(3), 521-530, 1996), the peptide Ser-Leu-Ile-Gly-Arg-Leu-OH (SEQ ID NO: 4) (hereinafter, referred to as "SLp-OH") in which a C-terminus of SLp-HN$_2$ is not amidated, the peptide trans-cinnamoyl-Leu-Ile-Gly-Arg-Leu-ornithine-NH$_2$ (SEQ ID NO: 2) (hereinafter, referred to as "tcLp-NH$_2$") (Hollenberg, M. D. et al., Can J Physiol Pharmacol, 75, 832-41, 1997) which is reported to specifically activate PAR-2, and the like. Furthermore, an antibody to PAR-2 or its fragment may also serve as a protein or a peptide which activates PAR-2 specifically.

The ingredient which activates PAR-2 may be obtained by screening various substances for the ability to activate PAR-2, according to any of the known methods. For example, the substance which binds to PAR-2 may be screened by directly detecting the interaction between PAR-2 and a test substance using labeling with a radioisotopic element, surface plasmon resonance or the like. A substance that induces signal transmission via PAR-2 may be screened using as an index of the biological activity caused by activation of PAR-2 in the cell or tissue expressing PAR-2. Further, the substance which has the gastric acid secretion inhibiting activity, the mucus promoting activity or the mucosa protecting activity, can be screened using a method for measuring an amount of gastric acid secretion, an amount of mucus secretion or the mucosa protecting activity shown in Examples. An assay for activation of PAR-2 is described in, for example, Hollenberg, M. D., Can. J. Physiol. Pharmacol., 75, 832-841, 1997 and Kawabata, A., J. Pharmacol. Exp. Ther., 288, 358-370, 1999. A method for screening a substance (i.e. agonist) which binds to and acts on a receptor is well-known in the art (see, for example, Hollenberg, M. D., Trends Pharmacol. Sci., 20, 271-273, 1999 Dery, O., Am. J. Physiol., 274, C1429-C1452, 1998 Kawabata, A.,J. Pharmacol. Exp. Ther., 288, 358-370, 1990).

As used herein, the term "peptide" refers to an oligopeptide and a relatively short polypeptide. The peptide contains, for example, 2-40 amino acid residues, preferably 3-20 amino acid residues, and more preferably, 5-15 amino acid residues. The peptide may be naturally occurring or may be chemically synthesized. The peptide may be synthesized according to the known method described in, for example, Carpino, L. A. et al., J. Org. Chem., 37,3404-3409, 1972. Alternatively, the peptide may be produced using the recombinant DNA technology. Furthermore, the peptide may contain modified or non-natural amino acid residues.

As used herein, the term "protein" refers to a longer polypeptide as compared with the peptide. The protein may be purified from a natural source, or may be produced by culturing a recombinant host cell containing a DNA encoding this protein. The protein may be chemically synthesized as well as the peptide. The protein may contain modified or non-natural amino acid residues.

Thus, since the ingredient which activates PAR-2 inhibits the gastric acid secretion, promotes the gastric mucus secretion, and also has the mucosa protecting activity, a composition containing the ingredient which activates PAR-2 of the invention is useful as a composition for inhibiting the gastric acid secretion, a composition for promoting the digestive mocus secretion, a composition for repairing a gastrointestinal tissue and a composition for protecting a gastrointestinal mucosa, is useful as a composition for preventing and treating digestive organs disease, and especially useful for preventing and/or treating gastric ulcer, duodenal ulcer, gastritis, diarrhea, enteritis and the like.

When used as a preventive agent or a therapeutic agent, the composition of the invention may be used as it is or by various treatments such as on dilution with water and the like, and may be used by incorporating into a pharmaceutical, a quasi drug and the like.

In this case, although an amount of the ingredient which activates PAR-2 to be incorporated is suitably selected depending on a product, the amount in the case of a systemic preparation usually may be 0.001-50% by weight, especially, 0.01-10% by weight. The sufficient activity in the prevention or treatment may not be shown when the amount is less than 0.001%, and the properties such as stability, flavoring and the like may be deteriorated when the amount exceeds 50%.

The ingredient which activates PAR-2 contained in the composition of the invention may be contained in a preparation as a pharmaceutically acceptable salt. Examples of the pharmaceutically acceptable salt include salts with a base such as an inorganic base, an organic base and the like, and an acid addition salt such as an inorganic acid, an organic acid, a basic or acidic amino acid and the like. Examples of the inorganic base contain an alkali metal such as sodium, potassium and the like, an alkaline-earth metal such as calcium, magnesium and the like, aluminum, ammonium, and the like. The organic base contains, for example, a primary amine such as ethanolamine and the like, a secondary amine such as diethylamine, diethanolamine, dicyclohexylamine, N,N'-dibenzylethylene-diamine and the like, a tertiary amine such as trimethylamine, triethylamine, pyridine, picoline, triethanolamine, and the like. Examples of the inorganic acid include hydrochloric acid, hydrobromic acid, nitric acid, sulfuric acid, phosphoric acid and the like. Examples of the organic acid include formic acid, acetic acid, lactic acid, trifluoroacetic acid, fumaric acid, oxalic acid, tartaric acid, maleic acid, benzoic acid, citric acid, succinic acid, malic acid, methanesulfonic acid, ethanesulfonic acid, benzenesulfonic acid, p-toluenesulfonic acid and the like. Examples of the basic amino acid include arginine, lysine, ornithine and the like. Examples of the acidic amino acid include aspartic acid, glutamic acid and the like.

When a peptide or a protein is used as the ingredient which activates PAR-2, since the peptide or the protein is degraded by peptidase present in the living body, the durability of the activity of activating PAR-2 can be enhanced by combination by using together with or incorporating therein a drug such as amastatin which is a peptidase inhibitor. When the aforementioned ingredient is not a peptide, those skilled in the art can suitably identify the substance for inactivating or degrading the ingredient, select an inhibitory substance which inhibits a substance for inactivating or degrading the ingredient, and use or incorporate therein the substance.

As a method of administering the composition of the present invention, in addition to oral and intravenous administration, transmucosal, transcutaneous, intramuscular, subcutaneous, intrarectal administration or the like can be suitably selected, and the composition can be used as various preparations depending on the method of administration.

Respective preparations will be described below. The preparation types used in the invention are not limited to them, but the composition may be used as various preparations usually used in the field of pharmaceutical preparation.

When used as a preventive or therapeutic drug for digestive organs disease, a dose of oral administration of the ingredient which activates PAR-2 is preferably in a range of 3-300 mg/kg, more preferably 10-100 mg/kg. When administered systemically, in particular, by intravenous administration, a dose varies depending upon age, sex, body type and the like, the preparation should be administered so that an effective blood concentration is preferably in a range of 2-200 µg/mL, more preferably 5-100 µg/mL.

As a dosage form in the case of oral administration, there are powders, granules, capsules, pills, tablets, elixirs, suspensions, emulsions, syrups and the like, and these dosage forms may be selected suitably. Moreover, these preparations may be subjected to modification such as sustained-release, stabilization, easy disintegration, poor disintegration, enteric coating, easy absorption and the like. Moreover, as a dosage form in the case of local administration in oral cavity, there are chewable preparations, sublingual preparations, buccal preparations, troches, ointments, patchs, solutions and the like, and these preparations may be selected suitably. These preparations may be also subjected to modification such as sustained-release, stabilization, easy disintegration, poor disintegration, enteric coating, easy absorption and the like.

For each dosage form described above, the technology of the known drug delivery system (DDS) may be adapted. As used herein, the "DDS preparation" refers to a preparation made in an optimal form of preparation, such as a sustained-release preparation, a preparation for local application (troches, buccal preparations, sublingual preparations etc.), a controlled release preparation, an enteric coated preparation, a non enteric coated preparation and the like after taking into consideration a route of administration, bioavailability, side effects and the like.

The constituent elements of DDS consist fundamentally of a drug, a drug-release module, a coating and a therapeutic program and, for each of constituent elements, especially, a drug with short half-life which reduces the blood concentration rapidly when release is stopped is preferable, a coating which does not react with the organism tissue at an administration site is preferable, and further a therapeutic program which maintains the optimal drug concentration during a set period is preferable. The drug-release module has fundamentally a drug reservoir, a release controlling part, an energy source, and a releasing pore or surface. All of these fundamental constituent elements are not necessary to exist together, and an optimal preparation may be selected by suitably adding or deleting some elements.

There are polymers, cyclodextrin derivatives, lecithin and the like as a material which may be used in DDS. Examples of the polymers include insoluble polymers (silicone, ethylene-vinyl acetate copolymer, ethylene-vinyl alcohol copolymer, ethyl cellulose, cellulose acetate etc.), water-soluble polymers and hydroxyl gel forming polymers (polyacrylamide, cross-linked polyhydroxyethyl methacrylate substance, cross-linked polyacrylate, polyvinyl alcohol, polyethylene oxide, a water-soluble cellulose derivative, a cross-linked poloxamer, chitin, chitosan etc.), slowly-soluble polymers (ethyl cellulose, a partial ester of methyl vinyl ether-maleic anhydride copolymer etc.), non-enteric coating polymers (hydroxypropylmethyl cellulose and hydroxypropyl cellulose, sodium carmellose, macrogol, polyvinyl pyrrolidone, dimethylaminoethyl methacrylate-methyl methacrylate copolymer etc.), enteric polymers (hydroxypropylmethyl cellulose phthalate, cellulose acetate phthalate, hydroxypropylmethyl cellulose acetate succinate, carboxymethylethyl cellulose, acrylate polymer etc.), biodegradable polymers (thermocoagulating or cross-linked albumin, cross-linked gelatin, collagen, fibrin, polycyanoacrylate, polyglycolic acid, polylactic acid, poly($\beta$-hydroxyacetic acid), polycaprolactone etc.), and the polymers can be selected suitably depending on a dosage form.

Particularly, silicone, ethylene-vinyl acetate coplymer, ethylene-vinyl alcohol copolymer, a partial ester of methyl vinyl ether-maleic anhydride may be used in a controlled-release of drug, cellulose acetate may be used as a material for an osmotic pressure pump, ethyl cellulose, hydroxypropylmethyl cellulose, hydroxypropyl cellulose and methyl cellulose may be used as a membrane material for a controlled release preparation, and cross-linked polyacrylate may be used as an adhesive agent for oral or ophthalmic mucosa.

Moreover, preparations may be produced by adding an additive, such as a solvent, a vehicle, a coating agent, a base, a binder, a lubricant, a disintegrant, a solution adjuvant, a suspending agent, a viscosity-increasing agent, an emulsifying agent, a stabilizer, a buffer, a tonicity agent, a soothing agent, a preservative, a flavoring agent, an aroma, a colorant and the like, depending on their dosage forms (the known preparation such as oral preparations, injections, suppositories etc.)

The following embodiments for each of these additives are exemplified, being not particularly limited.

Solvents: purified water, water for injection, physiological saline, peanut oil, ethanol, and glycerin;

Vehicles: starch, lactose, glucose, sucrose, microcrystalline cellulose, calcium sulfate, calcium carbonate, talc, titanium oxide, trehalose, and xylitol;

Coating agents: sucrose, gelatin, cellulose acetate phthalate, and the aforementioned polymers;

Bases: vaseline, vegetable oil, macrogol, oil in water type emulsion base, water in oil type emulsion base;

Binders: starch and derivatives thereof, cellulose and derivatives thereof, naturally-occurring high molecular compounds such as gelatin, sodium alginate, tragacanth, acacia and the like, synthetic high molecular compounds such as polyvinyl pyrrolidone, dextrin, and hydroxypropyl starch;

Lubricants: stearic acid and salts thereof, talc, wax, wheat starch, macrogol, hydrogenated vegetable oil, sucrose fatty acid ester, and polyethylene glycol;

Disintegrants: starch and derivatives thereof, gelatin, gelatin powder, sodium bicarbonate, cellulose and derivatives thereof, calcium carmellose, hydroxypropyl starch, carboxymethyl cellulose and salts and cross-linked materials thereof, and low-substituted types of hydroxypropyl cellulose;

Solution adjuvants: cyclodextrin, ethanol, propylene glycol, and polyethylene glycol;

Suspending agents: acacia, tragacanth, sodium alginate, aluminium monostearate, citric acid, and various surfactants;

Viscosity-increasing agents: sodium carmellose, polyvinyl pyrrolidone, methyl cellulose, hydroxypropylmethyl cellulose, polyvinyl alcohol, tragacanth, acacia, and sodium alginate;

Emulsifying agents: acacia, cholesterol, tragacanth, methylcellulose, various surfactants, lecithin;

Stabilizers: sodium hydrogensulfite, ascorbic acid, tocopherol, chelating agent, inert gas, and reducing substance;

Buffers: sodium hydrogenphosphate, sodium acetate, and boric acid;

Tonicity agents: sodium chloride, and glucose;

Soothing agents: procaine hydrochloride, lidocaine, benzyl alcohol;

Preservatives: benzoic acid and salts thereof, para-oxybenzoic acid esters, chlorobutanol, invert soap, benzyl alcohol, phenol, and thimerosal;

Flavoring agents: sucrose, saccharin, glycyrrhiza extract, sorbitol, xylitol, and glycerin;

Aromas: orange peel tincture and rose oil; and

Colorants: water-soluble food pigment, and lake pigment.

As described above, effects such as the durability the effective blood concentration of a drug and improvement in bioavailability can be expected by formulating a pharmaceutical into a DDS preparation such as sustained release preparation, enteric-coated preparation, controlled-release preparation or the like. However, an ingredient which activates PAR-2 is inactivated or degraded in a living body, consequently, the desired effect may be decreased or eliminated. For example, it is known that, when the ingredient which activates PAR-2 is a peptide, many of such the peptides will be degraded by aminopeptidase in the living body (Godin, D. et al., Eur. J. Pharmacol., 253, 225-30, 1994). Therefore, the effect of the ingredient may be further sustained by using an inhibitory substance which inhibits an activity of substance for inactivating or degrading the ingredient which activates PAR-2 (e.g., an inhibitory substance for inhibiting aminopeptidase) together with the composition of the invention.

As an aminopeptidase inhibitor, amastatin, arphamenine A, arphamenine B, bestatin and the like are known. These compounds may be incorporated into a preparation, or may be separately administered. When the aforementioned ingredient is not a peptide, those skilled in the art can suitably identify the substance for inactivating or degrading the ingredient, select an inhibitory substance which inhibits an activity of substance for inactivating or degrading the ingredient, and use or incorporate therein the substance.

In a preparation, ingredients used for usual compositions as additives other than the aforementioned additives may be used, and amounts of these ingredients to be added may be usual amounts in such a range that does not interfere with the effect of the present invention.

The composition of the present invention may be also used together with other ingredients in the treatment for disinfecting *Helicobacter Pylori*. For example, in addition to 40 mg (b.i.d.) of omepurazol and 1,500 mg (t.i.d.) of amoxycillin, 300 mg (t.i.d.) of the composition of the present invention may be used together.

The present composition is also useful for treating intractable digestive tract disorder, such as chronic peptic ulcer, ulcerative colitis observed in many young men or women, Crohn's disease and the like.

Then, the present invention will be explained in more detail by way of Examples, but the present invention is not limited to them.

EXAMPLES

Example 1

Method for Synthesizing Various Peptides

An agonist peptide (Ser-Leu-Ile-Gly-Arg-Leu-$NH_2$ (SLp-$NH_2$)) and a control peptide (Leu-Ser-Ile-Gly-Arg-Leu-$NH_2$ (LSp-$NH_2$)) used in Examples were synthesized according to the known method (Carpino, L. A. et al., J. Org. Chem., 37, 3404-3409, 1972).

Synthesis of Ser-Leu-Ile-Gly-Arg-Leu-$NH_2$ (SEQ ID NO: 1, SLp-$NH_2$)

1.33 g (0.17 meq/g) of Fmoc-PAL-PEG-PS-resin (PE BIOSYSTEMS) was weighted, and then 10 mL of dimethylformamide was added thereto to stand for 2 to 3 hours after the resin was expanded and filled into a column for synthesizing a peptide.

283 mg of Fmoc-L-Leu-OH (WAKO), 519 mg of Fmoc-L-Arg(Pbf)-OH (PE BIOSYSTEMS), 238 mg of Fmoc-L-Gly-OH (BACHEM), 283 mg of Fmoc-L-Ile-OH (WAKO), 283 mg of Fmoc-L-Leu-OH (WAKO) and 307 mg of Fmoc-L-Ser(tBu)-OH (PE BIOSYSTEMS) were weighted in test tubes, and each 380 mg of HATU(O-(7-azabenzotriazole-1-yl)-1,1,3,3-tetramethyl-uroniumhexa-fluorophosphate) (PE BIOSYSTEMS) was added to each test tube. The aforementioned amino acids were arranged in an order from a C-terminus, and synthesis was performed using peptide synthesizer PIONEER (PE BIOSYSTEMS). After the synthesized peptide-resin was treated with a mixed solution of TFA-$H_2$O-phenol-triisopropylsilane (8.8: 0.5: 0.5: 0.2) for 3 hours, the resin was filtered, and then the filtrate was recrystallized from ether to give a crude peptide. The crude peptide was then purified by subjecting to HPLC (A: 0.02% TFA containing $H_2$O, B: 0.02% TFA containing 50% $CH_3$CN). The resulting fraction was lyophilized to give Ser-Leu-Ile-Gly-Arg-Leu-$NH_2$.

Leu-Ser-Ile-Gly-Arg-Leu-$NH_2$ (SEQ ID NO: 5, LSp-$NH_2$)

LSp-$NH_2$ becomes an inactive substance by substituting Ser of SLp-$NH_2$ with Leu (Hollenberg, M. D., Trends Pharmacol. Sci., 17, 3-6, 1996, Nystedt, S. et al., Proc. Natl. Acad. Sci. USA, 91, 9208-12, 1994).

According to the procedure described above, a column for synthesizing a peptide was prepared, 283 mg of Fmoc-L-Leu-OH (WAKO), 519 mg of Fmoc-L-Arg(Pbf)-OH (PE BIOSYSTEMS), 238 mg of Fmoc-L-Gly-OH (BACHEM), 283 mg of Fmoc-L-Ile-OH (WAKO), 307 mg of Fmoc-L-Ser (tBu)-OH (PE BIOSYSTEMS) and 283 mg of Fmoc-L-Leu-OH (WAKO) were weighted in test tubes, and 380 mg of HATU was added to each test tube. The aforementioned amino acids were arranged in an order from a C-terminus, and synthesis was performed using a peptide synthesizer PIONEER (PE BIOSYSTEMS). According to the procedure described above, a crude peptide was obtained through the synthesized peptide-resin, and purified by subjecting to HPLC. The resulting fraction was lyophilized to give Leu-Ser-Ile-Gly-Arg-Leu-$NH_2$.

Moreover, trans-cinnamoyl-Leu-Ile-Gly-Arg-Leu-ornithine-$NH_2$ (SEQ ID NO: 2, tcLp-$NH_2$) also used in the Examples which is an agonist peptide was supplied from Professor Hollenberg M. D. in Medical Department of Calgary University.

For example, other various peptides which are a ingredient which activates PAR-2 are synthesized as follows:

Synthesis of Ser-Phe-Leu-Leu-Arg-$NH_2$ (SEQ ID NO: 3, SFp-$NH_2$)

1.33 g (0.17 meq/g) of the Fmoc-PAL-PEG-PS-resin (PE BIOSYSTEMS) was weighted, 10 mL of dimethylformamide was added thereto to stand for 2 to 3 hours, to expand a resin, and the resin is filled into a column for synthesizing a peptide.

519 mg of Fmoc-L-Arg(Pbf)-OH (PE BIOSYSTEMS), 283 mg of Fmoc-L-Leu-OH (WAKO), 283 mg of Fmoc-L-Leu-OH (WAKO), 305 mg of Fmoc-L-Phe-OH (WAKO), and 307 mg of Fmoc-L-Ser(tBu)-OH (PE BIOSYSTEMS) are weighted in test tubes, and 380 mg of HATU (PE BIOSYSTEMS) is added to each test tube. The aforementioned amino acids are arranged in an order from a C-terminus, and synthesis was performed using a peptide synthesizer PIONEER (PE BIOSYSTEMS). After the synthesized peptide-resin is treated with a mixed solution of TFA-$H_2$O-phenol-triisopropylsilane (8.8: 0.5: 0.5: 0.2) for 3 hours, the resin is filtered, and then the filtrate was recrystallized from ether to give a crude peptide. The crude peptide is then purified by subjecting to HPLC (A: 0.02% TFA containing $H_2$O, B: 0.02% TFA containing 50% $CH_3$CN). The resulting fraction can be lyophilized to give Ser-Phe-Leu-Leu-Arg-$NH_2$.

Synthesis of Ser-Leu-Ile-Gly-Arg-Leu-OH (SEQ ID NO: 4, SLp-OH)

1.00 g (0.21 meq/g) of Fmoc-L-Leu-PEG-PS-resin (PE BIOSYSTEMS) is weighted, 10 mL of dimethyl-formamide is added thereto to stand for 2 to 3 hours to expand a resin, and then the resin is filled into a column for synthesizing a peptide.

519 mg of Fmoc-L-Arg(Pbf)-OH (PE BIOSYSTEMS), 238 mg of Fmoc-L-Gly-OH (BACHEM), 283 mg of Fmoc-L-Ile-OH (WAKO), 283 mg of Fmoc-L-Leu-OH (WAKO), and 307 mg of Fmoc-L-Ser(tBu)-OH (PE BIOSYSTEMS) are weighted in test tubes, and 380 mg of HATU is added to each test tube. The aforementioned amino acids are arranged in an order from a C-terminus, and synthesis is performed using a peptide synthesizer PIONEER (PE BIOSYSTEMS). According to the procedure described above, a crude peptide is obtained through the synthesized peptide-resin and purified by subjecting to HPLC. The resulting fraction can be lyophilized to give Ser-Leu-Ile-Gly-Arg-Leu-OH.

Example 2

Influence on Acceleration of Carbachol-Induced Gastric Acid Secretion

Animal Used

In an experiment, male Wistar rats at 5 weeks of age were used. After each animal was pre-bred for one week under the circumstance of a room temperature of 23±2° C., the humidity of 50±5%, and the light-and-darkness cycle (light term: from 07:00 to 19:00) of 12 hours, each animal was subjected to the experiment. Water and solid feed were supplied freely during the pre-breeding period and the experiment period.

Moreover, the number of animals used in the experiment was 4-14 animals in all cases, and the results were shown by Mean±Standard Error. The significant difference test was performed by Tukey's multiple comparison test.

Method

A rat was anesthetized with ether after 18-24 hours of fasting, and an abdomen was incised by about 1 cm below a lower end of xiphoid sternum. Duodenum was pinched out of the opened abdominal hole, a part joining pylorus and duodenum was ligated, and the incised abdomen was sutured. After 30 minutes, the rat was exsanguinated to kill, the stomach was isolated, and gastric juice was collected. After the collected gastric juice was filtered, the acidity in the gastric juice was measured by a titration method. Carbachol (60 μg/kg) was administered subcutaneously immediately after pylorus ligation, and amastatin (2.5 μmol/kg) was administered intravenously at 1 min after carbachol administration, and SLp-$NH_2$ or LSp-$NH_2$ was administered intravenously at 1 min after amastatin administration, and then the effect on the gastric acid secretion accelerated by administration of carbachol was investigated.

Results

The results are shown in FIG. 1. In FIG. 1, a vertical axis shows an amount of secreted gastric acid (μmol/30 min), and a horizontal axis shows an administered drug and an amount thereof (V indicates administration of a vehicle). As shown in FIG. 1, SLp-$NH_2$ which is a PAR-2 agonist peptide inhibited dose-dependently the gastric acid secretion accelerated by administration of carbachol at a dose of 1.25 to 5 μmol/kg. To the contrary, LSp-$NH_2$ which is a control peptide for SLp-$NH_2$ did not affect the gastric acid secretion accelerated by carbachol at a dose of 5 μmol/kg.

Example 3

Influence on Mucin Secretion from Rat Gastric Mucosal Cells

Method

The gastric pylorus was ligated by the same procedure as described above. Amastatin (2.5 μmol/kg) was administered intravenously immediately after the ligation, and SLp-$NH_2$, LSp-$NH_2$ or tcLP-$NH_2$ was administered intravenously at 1 minute after administration of amastatin. 30 minutes after ligation, the rats was exsanguinated to kill, the stomach was isolated, and the gastric juice was collected. The collected sample of gastric juice was centrifuged at 10000×g for 30 min, and the supernatant was subjected to ultrafiltration with Millipore MC FREE (MW10000), followed by lyophilization. 2M TFA was added to the lyophilized sample, which was hydrolyzed under the conditions at 100° C. for 4 hours. Centrifugal separation was then performed and the supernatant was evaporated to dryness. 200 μL of 0.1 M Tris-HCl was added to the evaporated and dried sample to dissolve it. After 150 μL of a reaction solution containing galactose oxidase (1U), peroxidase (0.5 mU) and HPPA (0.25 μmol) was added to 50 μL of the sample and the mixture was incubated at 37° C. for 30 minutes, an amount of galactose was measured at an excitation wavelength of 320 nm and an fluorescence wavelength of 405 nm.

Results

Figure 2:
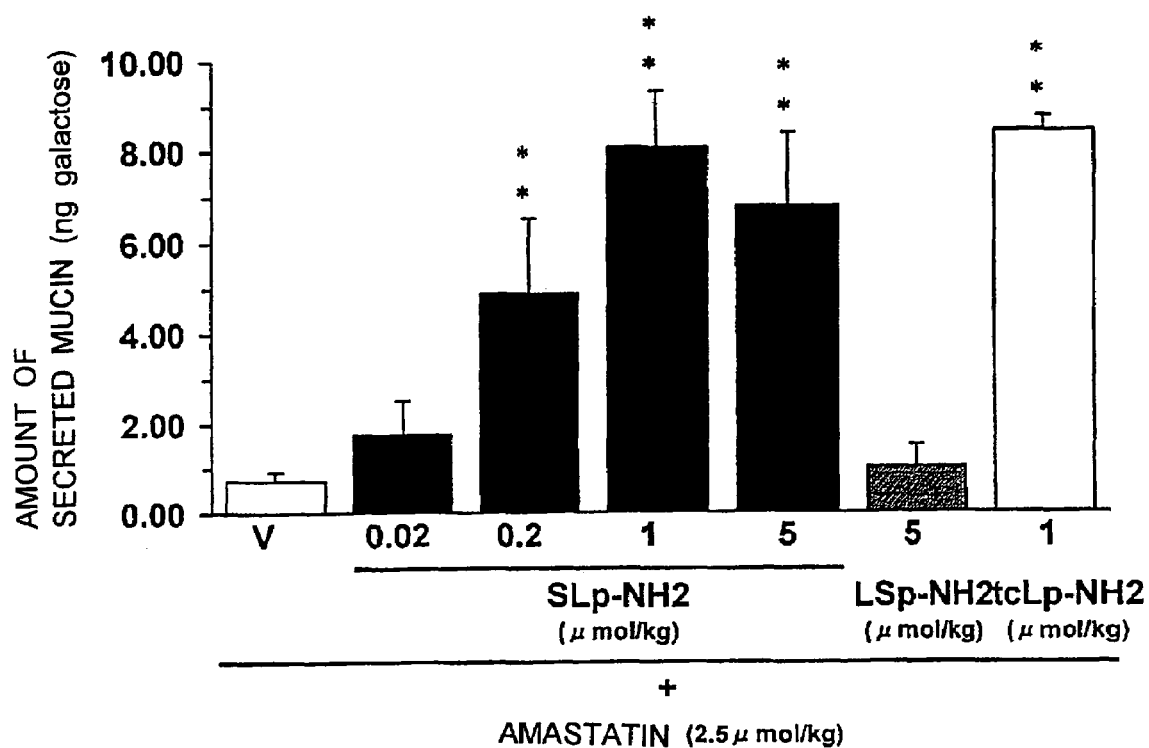
FIG. 2 is a view showing the effects of PAR-2 agonists peptide on secretion of mucin from gastric mucosa cells in vivo. ** $P<0.01$ vs. V (Tukey's test).

The results are shown in FIG. 2. In FIG. 2, a vertical axis shows an amount of secreted mucin (ng galactose), and a horizontal axis shows an administered drug and a dose thereof (V indicates the administration of a vehicle). As shown in FIG. 2, SLp-$NH_2$ accelerated dose-dependently the mucin secretion from rat gastric mucosal cells at a dose of 0.02 to 5 μmol/kg. The tcLp-$NH_2$, an agonist peptide which is more specific for PAR-2 than SLp-$NH_2$, also accelerated the mucin secretion like SLp-$NH_2$. To the contrary, LSp-$NH_2$ which is a control peptide for SLp-$NH_2$ did not affect mucin secretion.

Example 4

Influence on Ethanol- and Hydrochloric Acid-Ethanol-Induced Gastric Mucosa Lesion Method Preparation of ethanol- and hydrochloric acid-ethanol-induced gastric mucosa lesion was performed according to the method of Robert et al. (Robert, A. et al., Gastroenteral, 77, 433-443, 1979). That is, after the rats were fasted for 18 to 24 hours, 1 mL of 75% ethanol or 60% ethanol containing 150 mM hydrochloric acid was administered orally. Rats were exsanguinated to kill after 60 min and their stomachs were isolated. The isolated stomach was incised along with greater curvature, washed and fixed with 10% formaldehyde, and an area of gastric mucosa lesion was measured using Image analyzing software, Mac acpect (Mitani corporation, Chiba prefecture). SLp-$NH_2$ was administered intravenously at 5 minutes before administration of 75% ethanol or 60% ethanol containing 150 mM hydrochloric acid. Amastatin (2.5 μmol/kg) was administered at 1 minute before administration of SLp-$NH_2$.

Results

Figure 3:
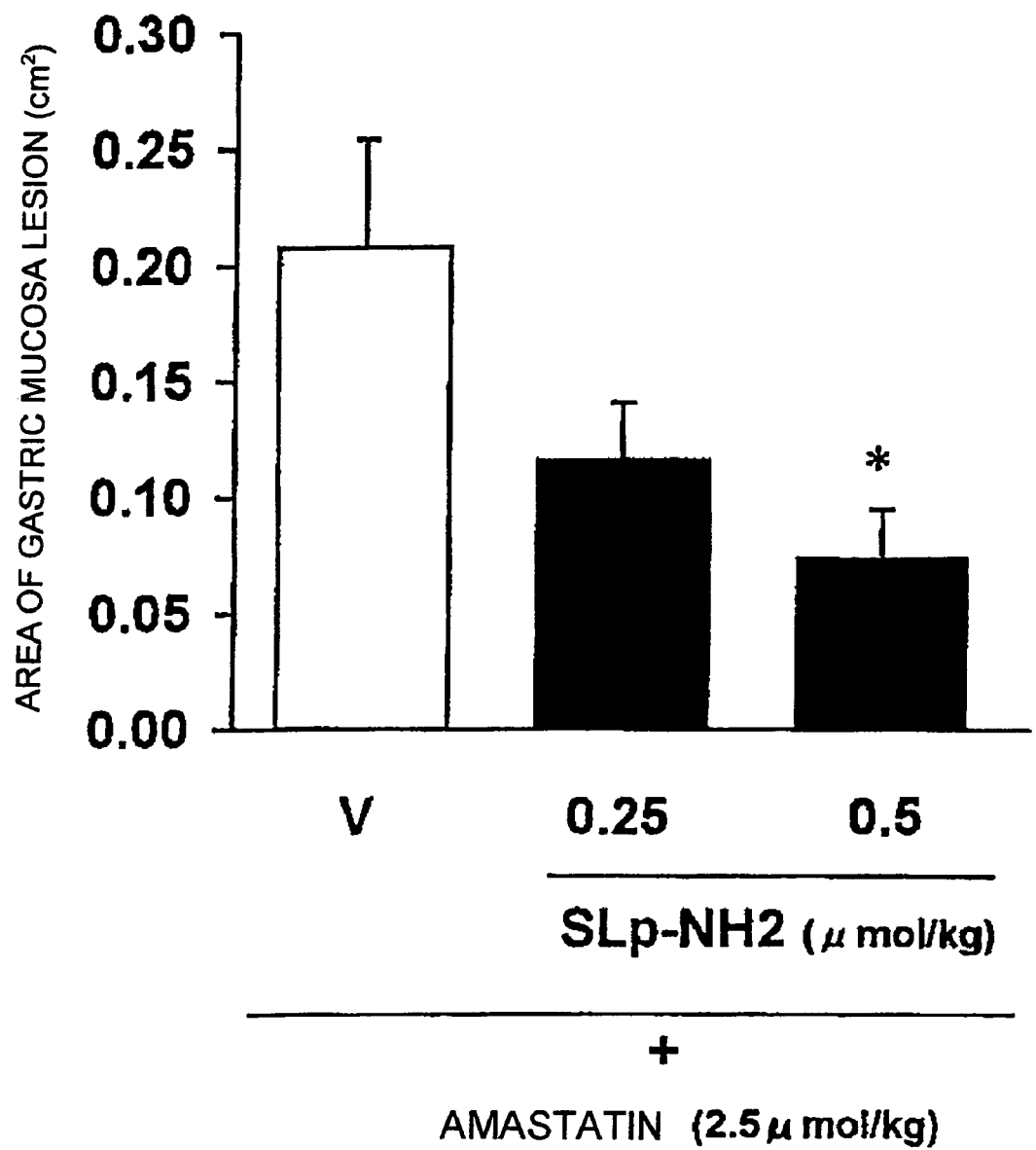
FIG. 3 is a view showing the effect of a PAR-2 agonist peptide on the lesion of gastric mucosa by ethanol in vivo. ** $P<0.01$ vs. V (Tukey's test).
Figure 4:
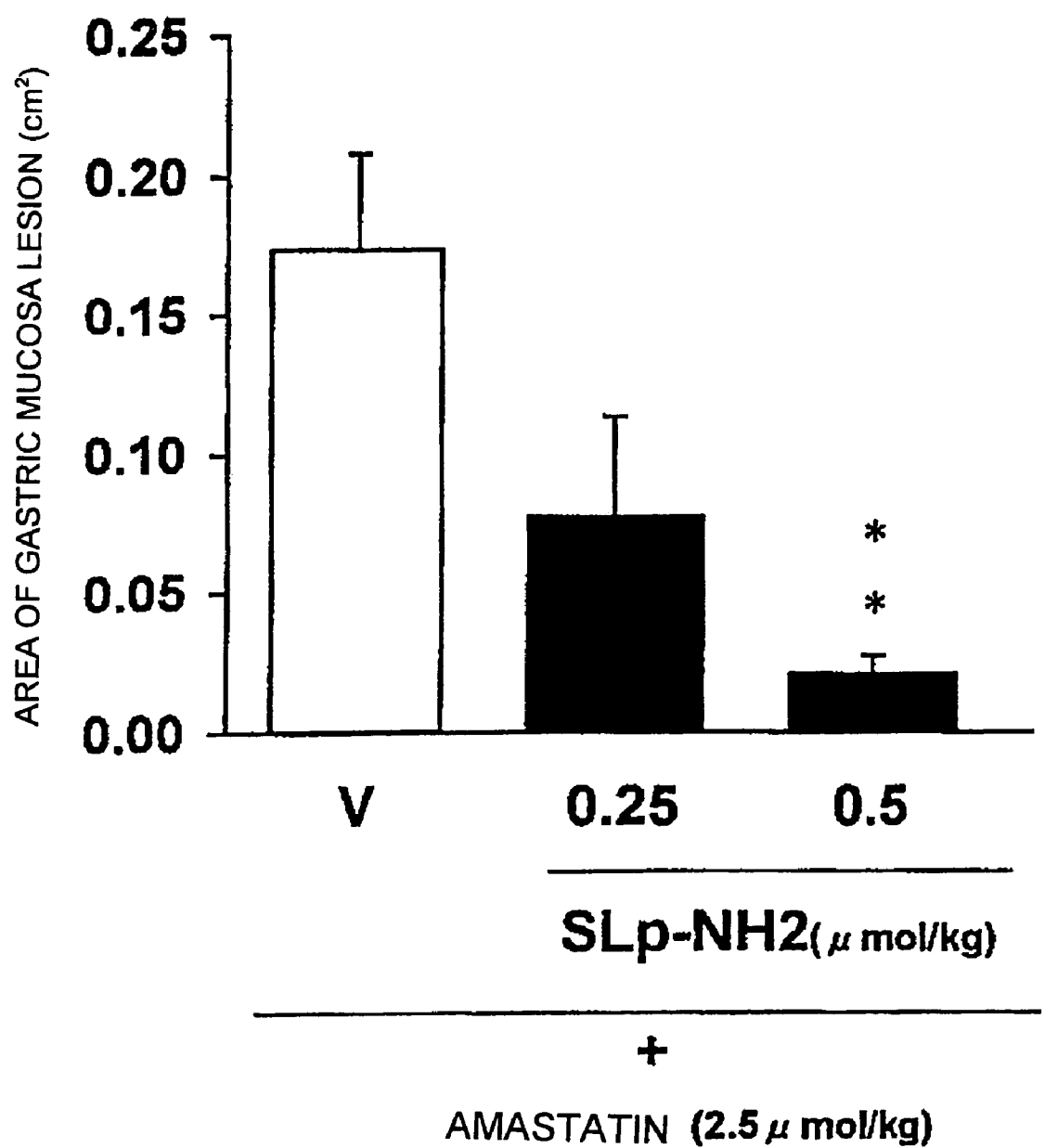
FIG. 4 is a view showing the effect of a PAR-2 agonist peptide on the lesion of gastric mucosa by hydrochloride-ethanol in vivo. ** $P<0.01$ vs. V (Tukey's test).

The results of administration of 75% ethanol are shown in FIG. 3, and the results of administration of 60% ethanol containing 150 mM hydrochloric acid are shown in FIG. 4. In FIGS. 3 and 4, a vertical axis shows the area ($cm^2$) of gastric mucosa lesion, and a horizontal axis shows an administered drug and a dose thereof (V indicates administration of a vehicle).

As shown in FIG. 3, SLp-$NH_2$ showed the protective effect on the gastric mucosa lesion by ethanol at a dose of 0.25 and 0.5 μmol/kg. As shown in FIG. 4, at a dose of 0.25 and 0.5 μmol/kg, the protective effect was shown also on the lesion in gastric mucosa by hydrochloric acid-ethanol as well as the lesion in gastric mucosa by ethanol.

Example 5

Tablet

A tablet was prepared by the conventional method according to the following formulation.

| | |
|---|---|
| Microcrystalline cellulose | 18 mg |
| SLp-$NH_2$ | 15 mg |
| Low-substituted hydroxypropyl cellulose | 12 mg |
| Hydroxypropylmethyl cellulose | 10 mg |
| Magnesium stearate | 1 mg |
| Lactose | q.s. |
| Total | 100 mg |

Example 6

Tablet

A tablet was prepared by the conventional method according to the following formulation.

| | |
|---|---|
| Amastatin | 20 mg |
| Microcrystalline cellulose | 18 mg |
| SLp-NH$_2$ | 15 mg |
| Low-substituted hydroxypropyl cellulose | 12 mg |
| Hydroxypropylmethyl cellulose | 10 mg |
| Magnesium stearate | 1 mg |
| Lactose | q.s. |
| Total | 100 mg |

Example 7

Capsule
A capsule was prepared by the conventional method according to the following formulation.

| | |
|---|---|
| SLp-NH$_2$ | 15 mg |
| Low-substituted hydroxypropyl cellulose | 15 mg |
| Closs-linked sodium carboxymethyl cellulose | 5 mg |
| Magnesium stearate | 2 mg |
| Lactose | 63 mg |
| Total | 100 mg |

Example 8

Capsule
A capsule was prepared by the conventional method according to the following formulation.

| | |
|---|---|
| SLp-NH$_2$ | 15 mg |
| Low-substituted hydroxypropyl cellulose | 15 mg |
| Amastatin | 5 mg |
| Closs-linked sodium carboxymethylcellulose | 5 mg |
| Magnesium stearate | 2 mg |
| Lactose | 63 mg |
| Total | 100 mg |

Example 9

Injection
An injection was prepared by the conventional method according to the following formulation.

| | |
|---|---|
| Glucose | 10 mg |
| SLp-NH$_2$ | 1 mg |
| Amastatin | 1 mg |
| Water for injection | q.s. |
| Total | 200 ml |

The preparations obtained in these Examples 5-9 may be used as a composition for inhibiting secretion of gastric acid, a composition for promoting secretion of digestive tract mucus, compositions for protecting digestive tract mucosa, and a composition for preventing or treating digestive organs diseases.

INDUSTRIAL APPLICABILITY

The composition of the invention is an excellent preventive or therapeutic drug having the gastric acid secretion inhibiting activity, the mucus secretion promoting activity, the mucosa protecting activity, the gastrointestinal tissue repairing activity and the like.

Therefore, digestive organs diseases can be effectively prevented and/or treated by using peptides Ser-Leu-Ile-Gly-Arg-Leu-NH$_2$, trans-cinnamoyl-Leu-Ile-Gly-Arg-Leu-ornithine-NH$_2$ and the like, which are an ingredient which activates PAR-2. Moreover, the durability of the activity of the aforementioned peptides can be enhanced by using together with or incorporating a drug such as peptidase inhibitor amastatin and the like, since the aforementioned peptides are degraded by peptidase present in the living body.

Sequence Listing Free Text

SEQ ID NO: 1: Designed peptide having PAR-2 agonist activity. The C-terminal amino acid residue is amidated.

SEQ ID NO: 2: Designed peptide having PAR-2 agonist activity. Xaa at 1 is trans-cinnamoyl-Leu. Xaa at 6 is Orn. The C-terminal amino acid residue is amidated.

SEQ ID NO: 3: Designed peptide having PAR-1 and PAR-2 agonist activity. The C-terminal amino acid residue is amidated.

SEQ ID NO: 4: Designed peptide having PAR-2 agonist activity. The C-terminal amino acid residue is hydroxylated.

SEQ ID NO: 5: Designed control peptide. The C-terminal amino acid residue is amidated.

What is claimed is:

1. A method for decreasing gastric acid secretion by activating PAR-2, comprising administering to a patient in need thereof an effective amount of a peptide comprising at least one sequence selected from the group consisting of Ser-Leu-Ile-Gly-Arg-Leu-NH$_2$ (SEQ ID NO: 1) and trans-cinnamoyl-Leu-Ile-Gly-Arg-Leu-ornithine-NH$_2$ (SEQ ID NO: 2).

2. A method for promoting gastrointestinal mucus secretion by activating PAR-2 comprising administering to a patient in need thereof an effective amount of a peptide comprising at least one sequence selected from the group consisting of Ser-Leu-Ile-Gly-Arg-Leu-NH$_2$ (SEQ ID NO: 1) and trans-cinnamoyl-Leu-Ile-Gly-Arg-Leu-ornithine-NH$_2$ (SEQ ID NO: 2).

3. A method for protecting gastrointestinal mucosa by activating PAR-2 comprising administering to a patient in need thereof an effective amount of a peptide comprising at least one sequence selected from the group consisting of Ser-Leu-Ile-Gly-Arg-Leu-NH$_2$ (SEQ ID NO: 1) and trans-cinnamoyl-Leu-Ile-Gly-Arg-Leu-ornithine-NH$_2$ (SEQ ID NO: 2).

4. A method for treating a digestive organ disease by activating PAR-2 comprising administering to a patient in need thereof an effective amount of a peptide comprising at least one sequence selected from the group consisting of Ser-Leu-Ile-Gly-Arg-Leu-NH$_2$ (SEQ ID NO: 1) and trans-cinnamoyl-Leu-Ile-Gly-Arg-Leu-ornithine-NH$_2$ (SEQ ID NO: 2).

5. The method of claim 4 wherein the digestive organ disease is at least one of gastric ulcer, duodenal ulcer, gastritis, diarrhea, or enteritis.

6. The method according to any of the claims 1-5 wherein said peptide is administered in conjunction with an inhibitory substance which inhibits inactivation or degrading of said peptide, and wherein said inhibitory substance is optionally combined with said peptide in a unit dosage form wherein said inhibitory substance is a peptidase inhibitor.

7. The method of claim 6 wherein said peptidase inhibitor is amastatin.

8. The method of any of claims 1-5, wherein said peptide is formulated into a drug delivery system (DDS) preparation.

9. The method of claim 6 wherein said peptide and/or said inhibitory substance are/is formulated into a drug delivery system (DDS) preparation.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial
<220> FEATURE:
<223> OTHER INFORMATION: Designed peptide having PAR-2 agonist
      activity. The C-terminal amino acid residue is amidated.
<220> FEATURE:
<221> NAME/KEY: AMIDATION
<222> LOCATION: (6)..(6)
```

```
<400> SEQUENCE: 1

Ser Leu Ile Gly Arg Leu
1               5

<210> SEQ ID NO 2
<211> LENGTH: 6
<212> TYPE: PRT
<213> ORGANISM: Artificial
<220> FEATURE:
<223> OTHER INFORMATION: Designed peptide having PAR-2 agonist
      activity. Xaa at 1 is trans-cinnamoyl-Leu. Xaa at 6 is Orn. The
      C-terminal amino acid residue is amidated.
<220> FEATURE:
<221> NAME/KEY: MOD_RES
<222> LOCATION: (1)..(1)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: AMIDATION
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Xaa Ile Gly Arg Leu Xaa
1               5

<210> SEQ ID NO 3
<211> LENGTH: 5
<212> TYPE: PRT
<213> ORGANISM: Artificial
<220> FEATURE:
<223> OTHER INFORMATION: Designed peptide having PAR-1 and PAR-2
      agonist activity. The C-terminal amino acid residue is amidated.
<220> FEATURE:
<221> NAME/KEY: AMIDATION
<222> LOCATION: (5)..(5)

<400> SEQUENCE: 3

Ser Phe Leu Leu Arg
1               5

<210> SEQ ID NO 4
<211> LENGTH: 6
<212> TYPE: PRT
<213> ORGANISM: Artificial
<220> FEATURE:
<223> OTHER INFORMATION: Designed peptide having PAR-2 agonist
      activity. The C-terminal amino acid residue is hydroxylated.
<220> FEATURE:
<221> NAME/KEY: MOD_RES
<222> LOCATION: (6)..(6)

<400> SEQUENCE: 4

Ser Leu Ile Gly Arg Leu
1               5

<210> SEQ ID NO 5
<211> LENGTH: 6
<212> TYPE: PRT
<213> ORGANISM: Artificial
<220> FEATURE:
<223> OTHER INFORMATION: Designed control peptide. The C-terminal
      amino acid residue is amidated.
<220> FEATURE:
<221> NAME/KEY: AMIDATION
```

```
-continued

<222> LOCATION: (6)..(6)

<400> SEQUENCE: 5

Leu Ser Ile Gly Arg Leu
1               5
```